(12) United States Patent
Feloney

(10) Patent No.: US 11,020,182 B1
(45) Date of Patent: Jun. 1, 2021

(54) TACTILE FEEDBACK FOR SURGICAL ROBOTS

(71) Applicant: Michael Feloney, Omaha, NE (US)

(72) Inventor: Michael Feloney, Omaha, NE (US)

( * ) Notice: Subject to any disclaimer, the term of this patent is extended or adjusted under 35 U.S.C. 154(b) by 1029 days.

(21) Appl. No.: 14/502,498

(22) Filed: Sep. 30, 2014

Related U.S. Application Data

(60) Provisional application No. 61/884,447, filed on Sep. 30, 2013.

(51) Int. Cl.
*A61B 5/00* (2006.01)
*A61B 19/00* (2006.01)
*A61B 17/00* (2006.01)

(52) U.S. Cl.
CPC ........... *A61B 19/2203* (2013.01); *A61B 2017/00026* (2013.01); *A61B 2017/00929* (2013.01); *A61B 2019/223* (2013.01); *A61B 2019/2223* (2013.01); *A61B 2019/2292* (2013.01)

(58) Field of Classification Search
CPC .......... A61B 18/1492; A61B 17/00234; A61B 2018/00077; A61B 19/2203; A61B 2019/223; A61B 2019/2292; A61B 2017/00929; A61B 2017/00026; A61B 2019/2223
USPC .................. 600/547, 564, 569, 570; 607/48; 606/161
See application file for complete search history.

(56) References Cited

U.S. PATENT DOCUMENTS

| | | | | |
|---|---|---|---|---|
| 4,483,133 A * | 11/1984 | Pasley | .................... | A01D 11/06 172/372 |
| 5,560,372 A * | 10/1996 | Cory | ........................ | A61B 5/05 600/547 |
| 5,800,350 A * | 9/1998 | Coppleson | ........... | A61B 5/0059 600/372 |
| 5,843,000 A * | 12/1998 | Nishioka | ................ | A61B 10/06 600/104 |
| 6,055,452 A * | 4/2000 | Pearlman | ............. | A61B 5/0536 600/547 |
| 6,584,348 B2 * | 6/2003 | Glukhovsky | ........ | A61B 5/0031 600/300 |
| 6,594,518 B1 * | 7/2003 | Benaron | .............. | A61B 5/0059 600/342 |
| 6,678,552 B2 * | 1/2004 | Pearlman | ............. | A61B 5/0536 600/547 |
| 6,845,264 B1 * | 1/2005 | Skladnev | ............. | A61B 5/0531 600/373 |
| 7,212,852 B2 * | 5/2007 | Smith | .................... | A61B 5/053 600/547 |
| 8,150,506 B2 * | 4/2012 | Kaushal | ................. | A61B 5/053 600/383 |
| 8,374,723 B2 * | 2/2013 | Zhao | ..................... | B25J 9/1689 318/568.11 |
| 8,417,328 B2 * | 4/2013 | Sarfaty | .................... | A61B 5/05 600/547 |

(Continued)

*Primary Examiner* — May A Abouelela
(74) *Attorney, Agent, or Firm* — Suiter Swantz pc llo

(57) ABSTRACT

A surgical instrument includes a pressure sensitive element that contacts a patient's tissue during surgery. The pressure sensitive element sends a signal to a computer processor that compares the signal to a known pressure being applied to the surgical instrument to calculate the rigidity of the tissue. The processor then delivers that information to the operating surgeon. The rigidity of the tissue may correspond to an audible tone, visual indicator or tactile feedback.

17 Claims, 13 Drawing Sheets

(56) References Cited

U.S. PATENT DOCUMENTS

| | | | | |
|---|---|---|---|---|
| 8,594,841 B2* | 11/2013 | Zhao | ................ | B25J 9/1633 |
| | | | | 318/566 |
| 2006/0030833 A1* | 2/2006 | Harris | ................ | A61B 5/0422 |
| | | | | 604/503 |
| 2006/0085049 A1* | 4/2006 | Cory | ................ | A61B 5/0536 |
| | | | | 607/48 |
| 2006/0116703 A1* | 6/2006 | Glaser | ................ | A61F 9/007 |
| | | | | 606/161 |
| 2010/0168561 A1* | 7/2010 | Anderson | ............ | A61B 90/36 |
| | | | | 600/424 |
| 2010/0228264 A1* | 9/2010 | Robinson | ........... | A61B 18/1206 |
| | | | | 606/130 |
| 2011/0054344 A1* | 3/2011 | Slizynski | ................ | A61B 5/053 |
| | | | | 600/547 |
| 2011/0082383 A1* | 4/2011 | Cory | ................ | A61B 5/0536 |
| | | | | 600/547 |
| 2012/0065539 A1* | 3/2012 | Slizynski | ................ | A61B 5/053 |
| | | | | 600/547 |
| 2013/0289767 A1* | 10/2013 | Lim | ................ | B25J 9/1633 |
| | | | | 700/253 |
| 2014/0005668 A1* | 1/2014 | Rhee | ............. | A61B 17/320092 |
| | | | | 606/45 |
| 2014/0005682 A1* | 1/2014 | Worrell | ............. | A61B 18/1442 |
| | | | | 606/130 |
| 2015/0224326 A1* | 8/2015 | Toth | ................ | A61B 5/042 |
| | | | | 600/301 |

* cited by examiner

TACTILE FEEDBACK FOR SURGICAL ROBOTS

PRIORITY

The present application claims the benefit under 35 U.S.C. § 119(e) of U.S. Provisional Application Ser. No. 61/884,447, filed Sep. 30, 2014, which is incorporated herein by reference.

FIELD OF THE INVENTION

The present invention is directed generally toward surgical robots and more particularly to sensory feedback mechanisms in surgical robots.

BACKGROUND OF THE INVENTION

Surgical robots allow surgeons to perform surgical procedures in a minimally invasive way. Existing camera technology gives the operating surgeon excellent visual feedback, and in some cases even stereoscopic 3D views of the operating area. However, surgical robots do not provide haptic or tactile information to the surgeon. Tactile information may be more important than visual information in many circumstances, especially to give the surgeon a more complete sense of where a surgical instrument is located with respect to surrounding tissue. Surgeons are used to using the resistance of surrounding tissue to inform their decisions during surgery. The lack of tactile information is a substantial loss for robotic based surgery.

Consequently, it would be advantageous if an apparatus existed that is suitable for providing tactile information to a surgeon operating a surgical robot.

SUMMARY OF THE INVENTION

Accordingly, the present invention is directed to a novel method and apparatus for providing tactile information to a surgeon operating a surgical robot.

In at least one embodiment, a surgical instrument adapted for use with a surgical robot includes a pressure sensitive element. The pressure sensitive element sends a signal to a computer processor. The computer processor compares the output signal to a known pressure being applied to the surgical instrument to calculate the rigidity of the tissue. The processor then delivers that information to the operating surgeon.

In at least one embodiment, the processor translates the rigidity of the tissue into an audible tone. The audible tone may be directly related to the rigidity of the tissue or to a type of tissue determined by the processor upon comparison of the calculated rigidity and a table of rigidity values for various tissues.

In another embodiment, a surgical instrument adapted for use with a surgical robot includes an element for applying an electrical current to a tissue. Conductivity may be used to determine the type of tissue.

In another embodiment, a surgical instrument adapted for use with a surgical robot includes an element for generating a sound at a precise, known frequency. A corresponding microphone may receive sound waves passing through a tissue and determine the type of tissue based on changes to the precise, known frequency.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

Figure 1:
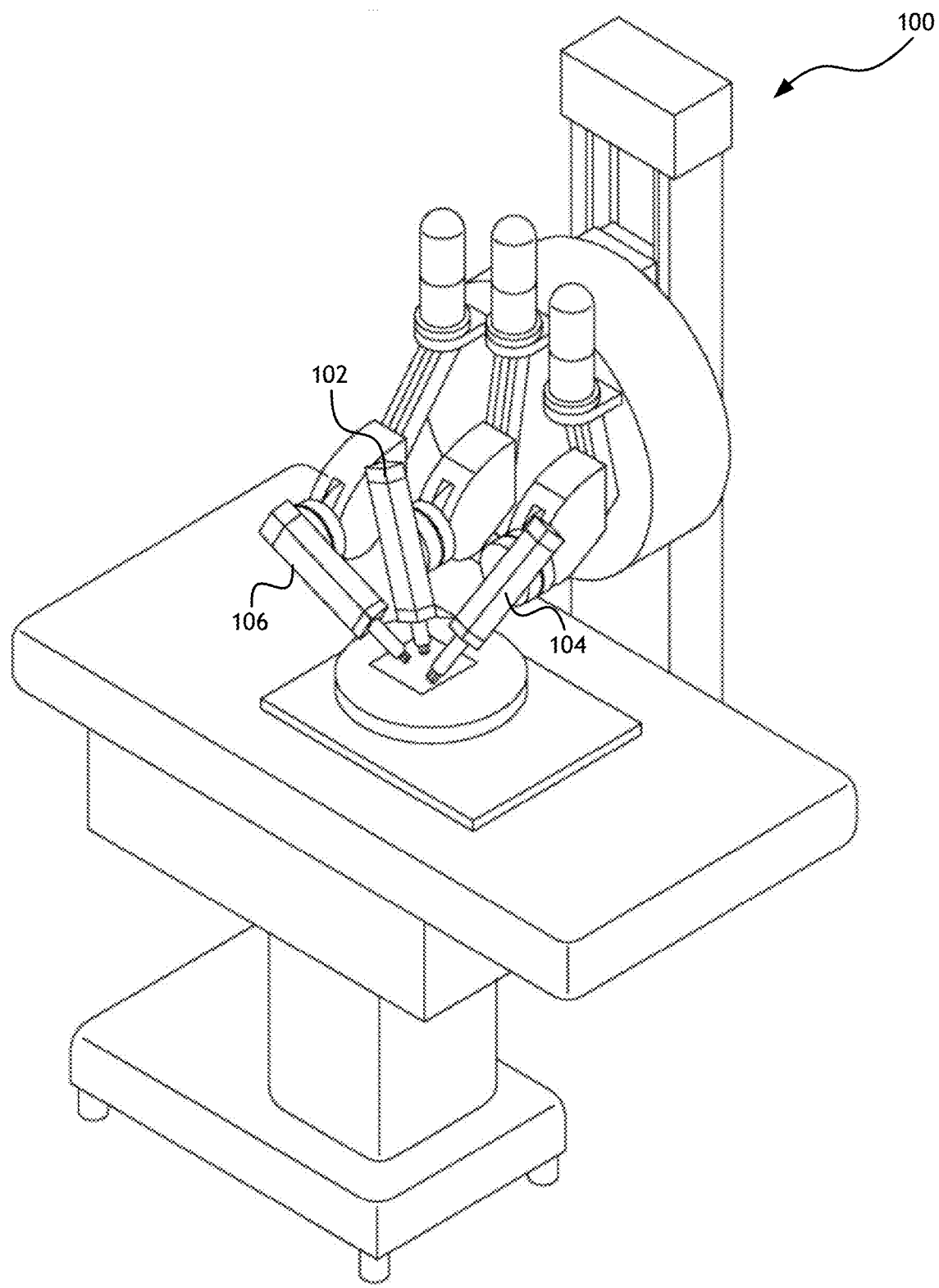
FIG. 1 shows an environmental view of a surgical robot including one embodiment of the present invention.

Referring to FIG. 1, an environmental view of a surgical robot 100 including one embodiment of the present invention is shown. A surgical robot 100 may include a plurality of instruments 102, 104, 106. In at least one embodiment, the plurality of instruments 102, 104, 106 includes a haptic feedback instrument 106. The haptic feedback instrument 106 contacts a tissue sample and determines the type of tissue. A computer system utilizing the surgical robot 100 may analyze signals from the haptic feedback instrument 106 with reference to known data corresponding to various human tissues. A haptic feedback instrument 106 may be affixed to another instrument 102, 104 adapted for a surgical robot 100. Alternatively, the haptic feedback instrument 106 may be an element of the surgical robot 100, configured to use with any surgical attachments.

Figure 2:
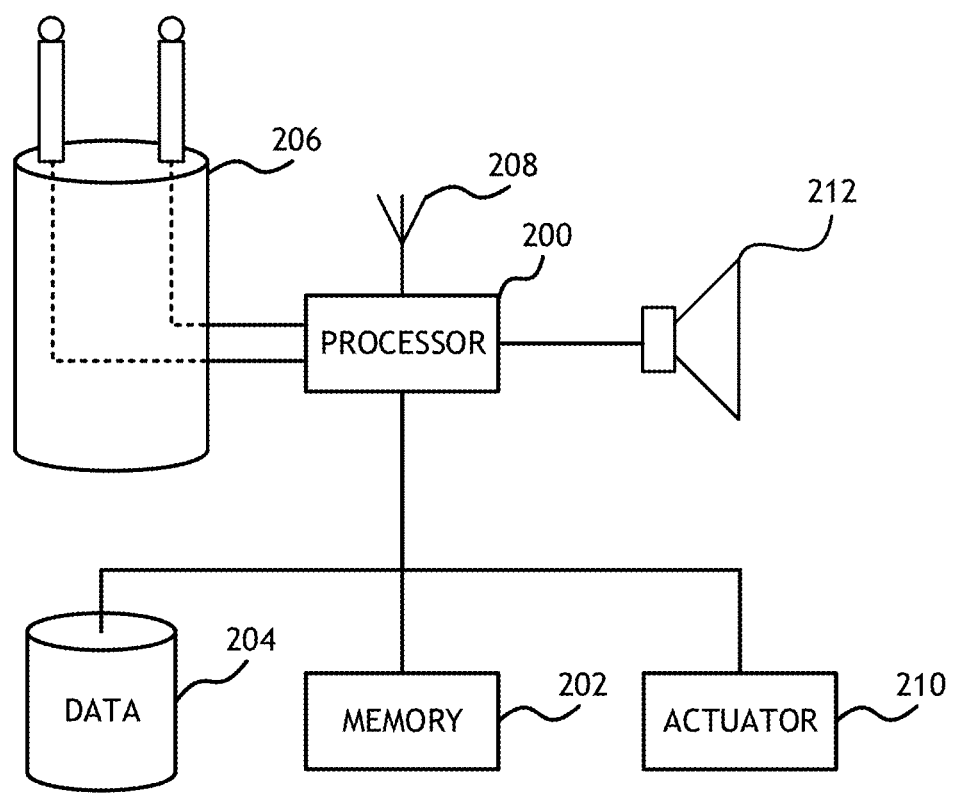
FIG. 2 shows a block diagram of a system according to one embodiment of the present invention.

Referring to FIG. 2, a block diagram of a system according to one embodiment of the present invention is shown. The system may include a haptic feedback instrument 206 configured to contact tissue during a surgical procedure. The haptic feedback instrument 206 is connected to a processor 200 executing computer executable program code stored in a memory 202. The processor 200 generates a known signal and applies the signal to the tissue through an actuator node and receives a corresponding output signal through a generator node.

In one embodiment, the processor 200 compares the output signal to a database 204 of known output signals corresponding to different tissue types. The processor 200 may then transmit such tissue data to a remote user through a data link connection 208. A remote user may receive feedback indicating the tissue type from one of a plurality of sources. In one embodiment, a remote processor 200 may include an indication of tissue type in a visual display. Alternatively, the local processor 200 may incorporate an indication of tissue type in a video data stream transmitted to the remote user through the data link connection 208.

In one embodiment, a processor 200 may apply one of a set of distinct audio signals to a speaker 212 indicating tissue type. In another embodiment, the processor 200 may apply one of a set of distinct signals to an actuator 210 or motor configured to provide force feedback to the remote user. Such force feedback may comprise a distinct set of pulses, a distinct pressure, or some other tactile indicator.

In another embodiment, the speaker 212 may generate a precise, known, directional sound frequency near a tissue of interest where the haptic feedback instrument 206 comprising a microphone receives sound waves passing through the tissue. The processor 200 then determines the type of tissue based on changes to the precise, known frequency.

A person skilled in the art may appreciate that while components are shown having a direct physical connection, components may be in data communication via data link connections 208 over substantial distances and with additional components interposed. For example, the processor 200 connected to the haptic feedback instrument 206 may be different from the processor 200 connected to the speaker 212 and actuator 210.

Figure 3:
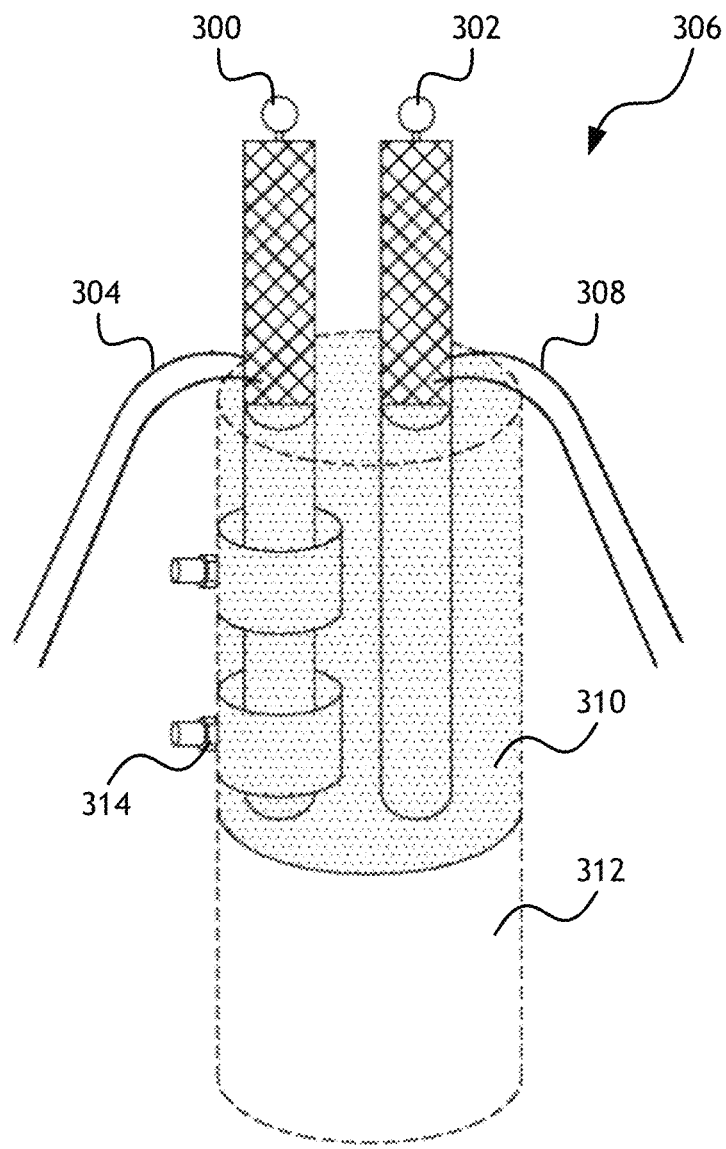
FIG. 3 shows a perspective view of one embodiment of the present invention.

Referring to FIG. 3, a perspective view of one embodiment of the present invention is shown. A pressure sensitive haptic feedback instrument 306 according to at least one embodiment of the present invention may include an actuator node 300 and a generator node 302. The actuator node 300 may comprise a piezoelectric material that vibrates according to a function defined by the size and shape of the actuator node 300 and the type of piezoelectric material, driven by an input signal 304.

Furthermore, the generator node 302 may also comprise a piezoelectric material that produces an output signal 308 according to a function defined by the size and shape of the generator node 302 and the type of piezoelectric material, driven by a vibration frequency.

In actual implementation, a known input signal 304 drives vibrations of the actuator node 300. The actuator node 300 is in contact with tissue during a surgical procedure and thereby imparts a vibration to the tissue. The generator node 302, also in contact with the tissue during the surgical procedure, receives a vibration generated by the actuator node 300, modified by properties of the tissue, and converts such vibration to the output signal 308.

In at least one embodiment, both the actuator node 300 and the generator node 302 include spherical tips for direct contact with the tissue.

The actuator node 300 may be isolated from the generator node 302 so that vibration transmission is limited to vibrations transmitted through a tissue sample. The actuator node 300 and generator node 302 may be embedded in an appropriate barrier material such as polydimethylsiloxane (PDMS). The actuator node 300 may be further isolated from the generator node 302 through one or more brackets 314.

Furthermore, the actuator node 300 and generator node 302 may be isolated from vibrations produced by the surgical robot through a Styrofoam plug 312.

In another embodiment, the actuator node 300 and/or the generator node 302 may produce a voltage by pressing against a tissue. The voltage produced compared to a known applied pressure may be a measure of the rigidity of the tissue, and therefore of the type of tissue.

In another embodiment, the actuator node 300 and the generator node 302 may be used to measure the conductivity of the tissue. Different conductivities of different tissues may be a measure of the type of tissue.

Figure 4:
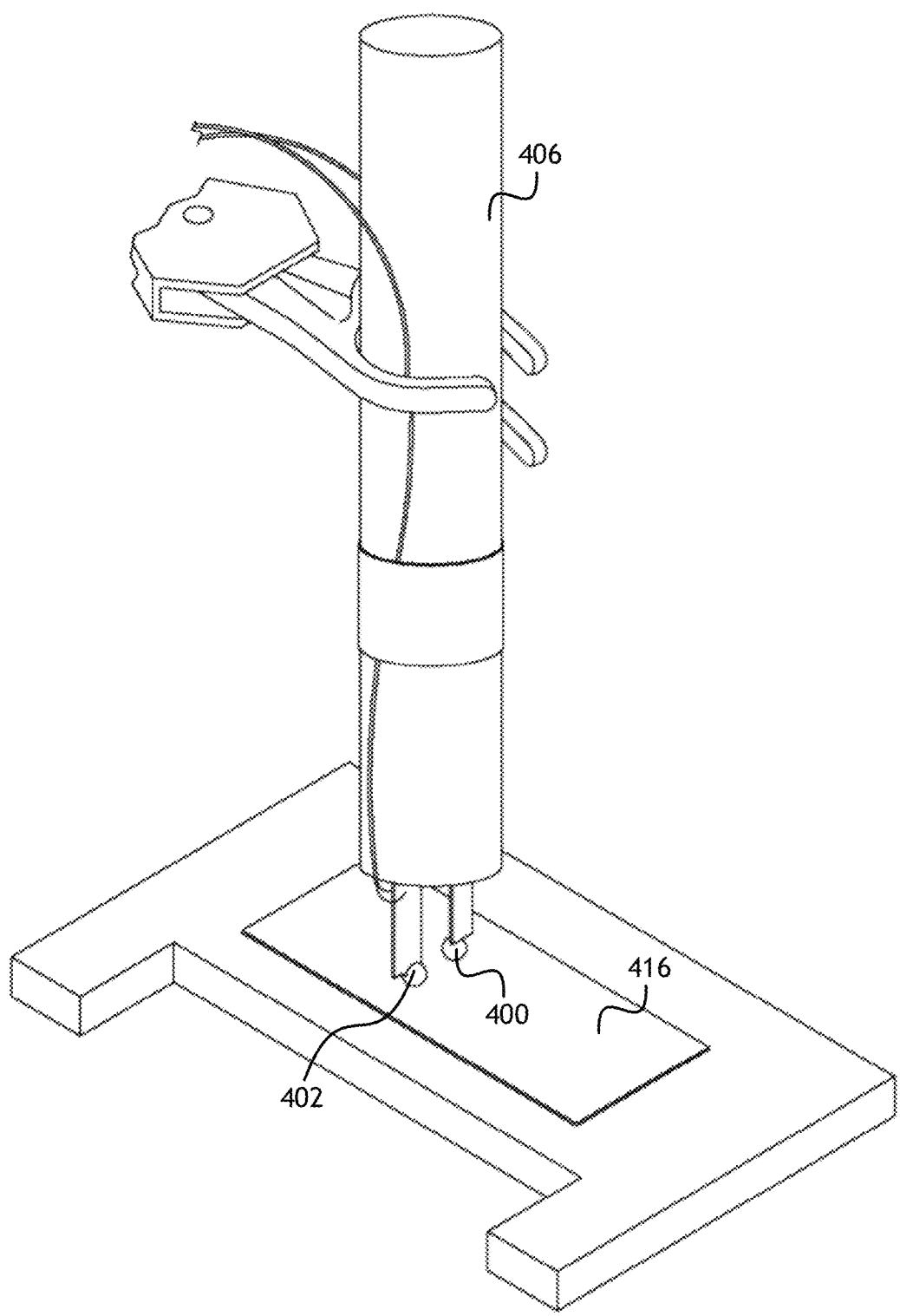
FIG. 4 shows an environmental view of one embodiment of the present invention.

Referring to FIG. 4, an environmental view of one embodiment of the present invention is shown. A haptic feedback instrument 406 having an actuator node 400 and a generator node 402 is placed in contact with a tissue 416. Vibrations are produced by the actuator node 400 via signals from a processor in a surgical robot and transmitted through the tissue 416 to the generator node 402. The generator node 402 converts the vibrations to an output signal corresponding to the tissue. A processor may receive the output signal and thereby identify the tissue 416.

A person skilled in the art may appreciate that even though FIG. 4 shows the haptic feedback instrument 406 in contact with a segregated tissue 416 sample, in actual implementation, the haptic feedback instrument 406 would contact tissue 416 inside a patient during a surgical procedure.

Figure 5:
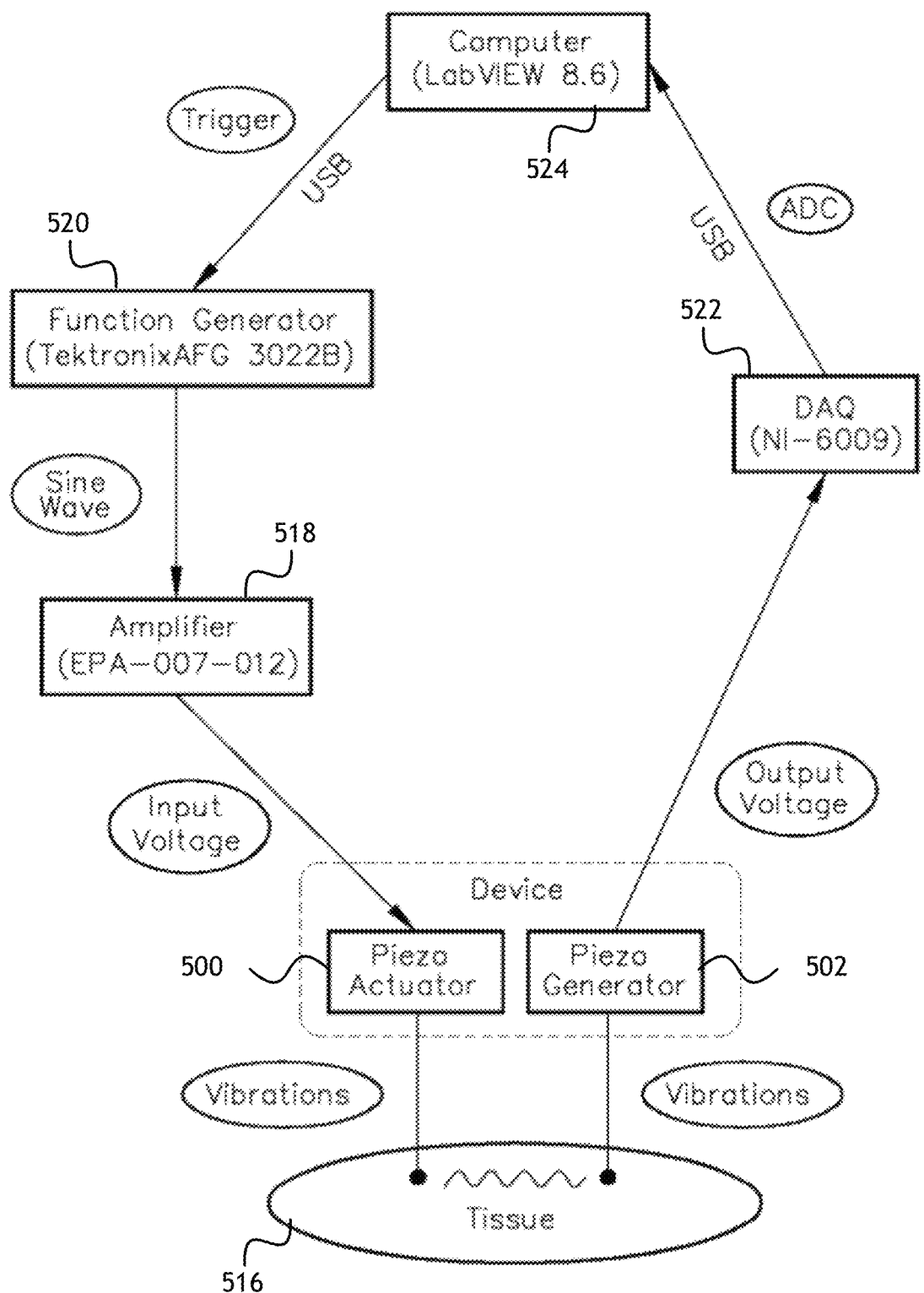
FIG. 5 shows a flowchart of a system according to at least one embodiment of the present invention.

Referring to FIG. 5, a flowchart of a system according to at least one embodiment of the present invention is shown. A computer 524 connected to a function generator 520 instructs the function generator 524 to produce a known signal. The signal may be amplified by an amplifier 518. The amplified signal drives a piezoelectric actuator node 500 to generate a known vibration. The piezoelectric actuator node 500 transmits the vibrations through a tissue 516 during a surgical procedure. The tissue 516 alters the vibrations according to the properties of the tissue 516, such as elastic modulus, and the altered vibrations drive a piezoelectric generator node 502 to produce an output voltage. The output voltage is received by a data acquisition device 522 which delivers the data to computer 524.

In one embodiment, the computer 524 compares the output voltage to a set of known voltages corresponding to different tissue samples. In another embodiment, the computer 524 compares the output voltage to the known signal, and determines the identity of the tissue 516 based on the difference between the output voltage and the known signal.

Furthermore, changing vibrations over time may provide further indication of the type of tissue 516. For example pulses due to blood flow may alter the vibrations.

The computer 524 may also incorporate additional information to distinguish types of tissue 516. For example, the computer 524 may receive visual data from a camera and incorporate a spectrographic element to further distinguish one tissue 516 from another. The computer 524 may refer to a database of tissue 516 properties to determine the type of tissue 516 and associated audible indicator.

Figure 6:
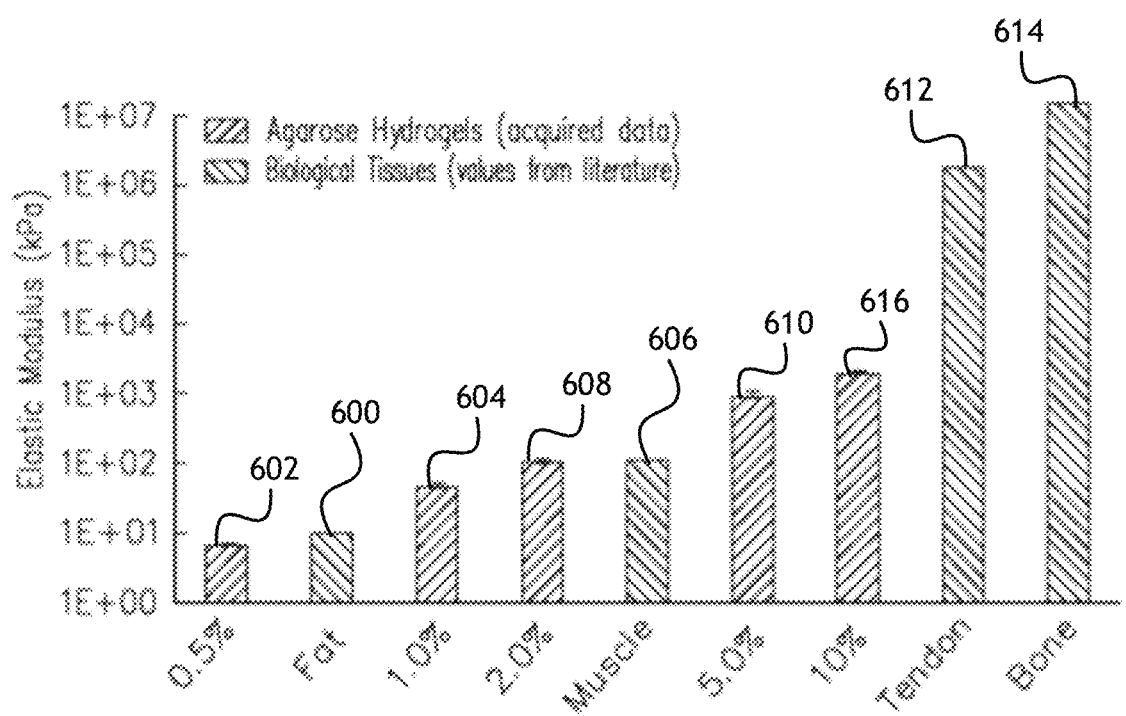
FIG. 6 shows a bar graph of data comparing known elastic moduli of various materials to tested values of hydrogels.

Referring to FIG. 6, a bar graph of data comparing known elastic moduli of various materials to tested values of hydrogels is shown. Natural biological materials such as fat 602, muscle 608, tendon 614 and bone 616 each have a distinct elastic modulus as measured in kilopascals (kPa). By comparison, the elastic modulus of hydrogels 600, 604, 606, 610, 612 at concentrations of 0.5%, 1.0%, 2.0%, 5.0% and 10% are shown. Hydrogels were used for testing of a haptic feedback instrument according to at least one embodiment of the present invention as various concentrations of hydrogels simulate various tissue densities. Certain tested variations show the correlation between the tested materials 600, 604, 606, 610, 612 and known, real values 602, 608, 614, 616, demonstrating the validity of the testing methodology.

Figure 7:
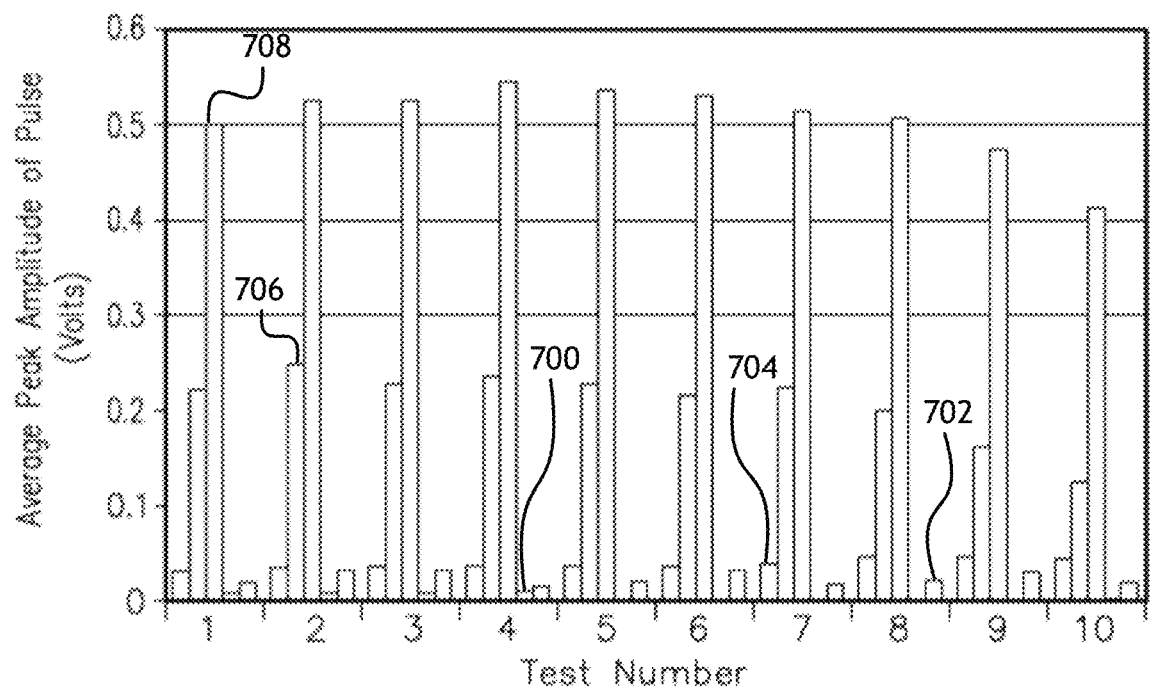
FIG. 7 shows a bar graph of average peak voltage produced by one embodiment of the present invention in various concentrations of hydrogels.

Referring to FIG. 7, a bar graph of average peak voltage produced by one embodiment of the present invention in various concentrations of hydrogels is shown. Ten tests, each comprising five pulses delivered by one embodiment of the present invention to hydrogels of various concentrations were recorded. Tested concentrations of hydrogels are ordered consistently between tests and only a single reference numeral is used to refer to each concentration to prevent obfuscation of the data.

A control group 700 of no hydrogel consistently showed the lowest average peak amplitude. Hydrogel concentrations of 0.5% 702, 1.0% 704, 2.0% 706 and 5.0% 708 tended to show increasing average peak amplitude as hydrogel concentration increased.

Figure 8:
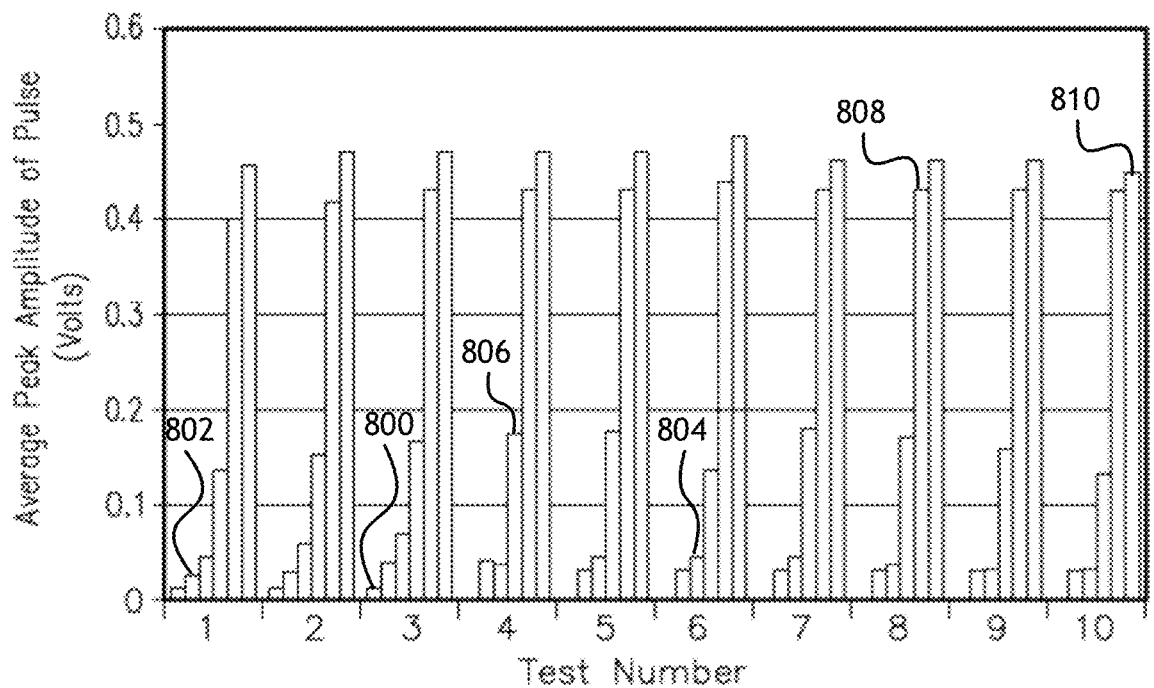
FIG. 8 shows a bar graph of average peak voltage produced by one embodiment of the present invention in various concentrations of hydrogels.

Referring to FIG. 8, a bar graph of average peak voltage produced by one embodiment of the present invention in various concentrations of hydrogels is shown. Ten tests, each comprising five pulses delivered by one embodiment of the present invention to hydrogels of various concentrations were recorded. Again, tested concentrations of hydrogels are ordered consistently between tests and only a single reference numeral is used to refer to each concentration to prevent obfuscation of the data.

A control group 800 of no hydrogel consistently showed the lowest average peak amplitude. Hydrogel concentrations of 0.5% 802, 1.0% 804, 2.0% 806, 5.0% 808 and 10% 810 tended to show increasing average peak amplitude as hydrogel concentration increased. A person skilled in the art may appreciate that the relation between hydrogel concentration and average peak amplitude may not be linear in nature and may be subject to statistical analysis to determine a relation and calibrate embodiments of the present invention.

Figure 9:
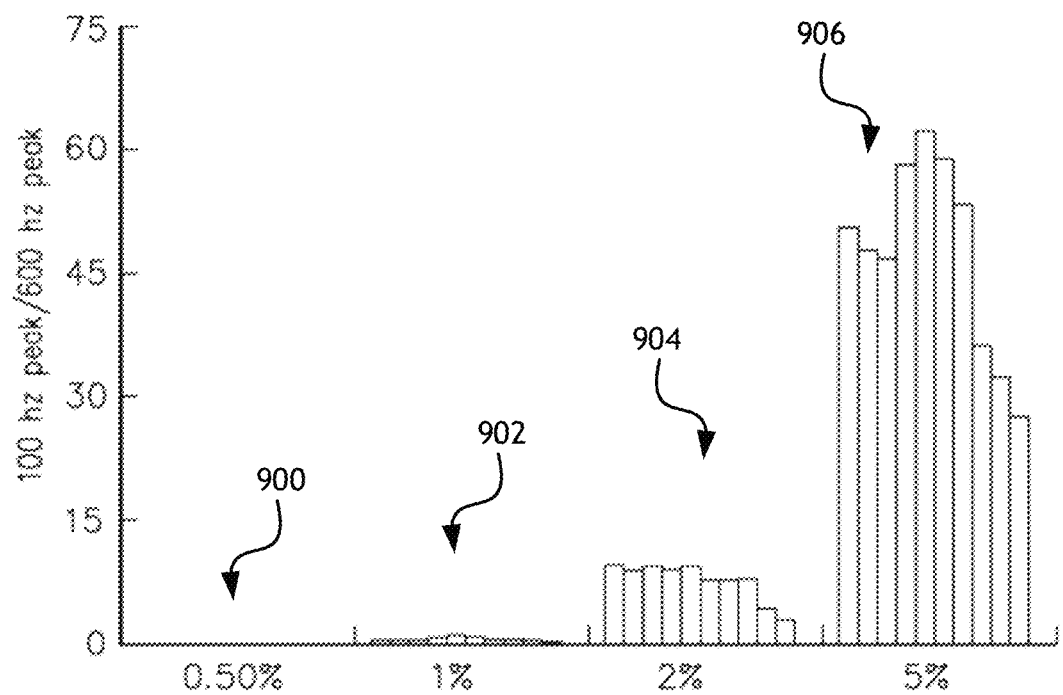
FIG. 9 shows a bar graph of vibration frequencies produced by one embodiment of the present invention in various hydrogel concentrations.

Referring to FIG. 9, a bar graph of vibration frequencies produced by one embodiment of the present invention in various hydrogel concentrations is shown. In ten tests, the vibrational frequencies of hydrogels of 0.5% 900, 1.0% 902, 2.0% 904 and 5.0% 906 were measured and found to generally increase as hydrogel concentrations increase.

Figure 10:
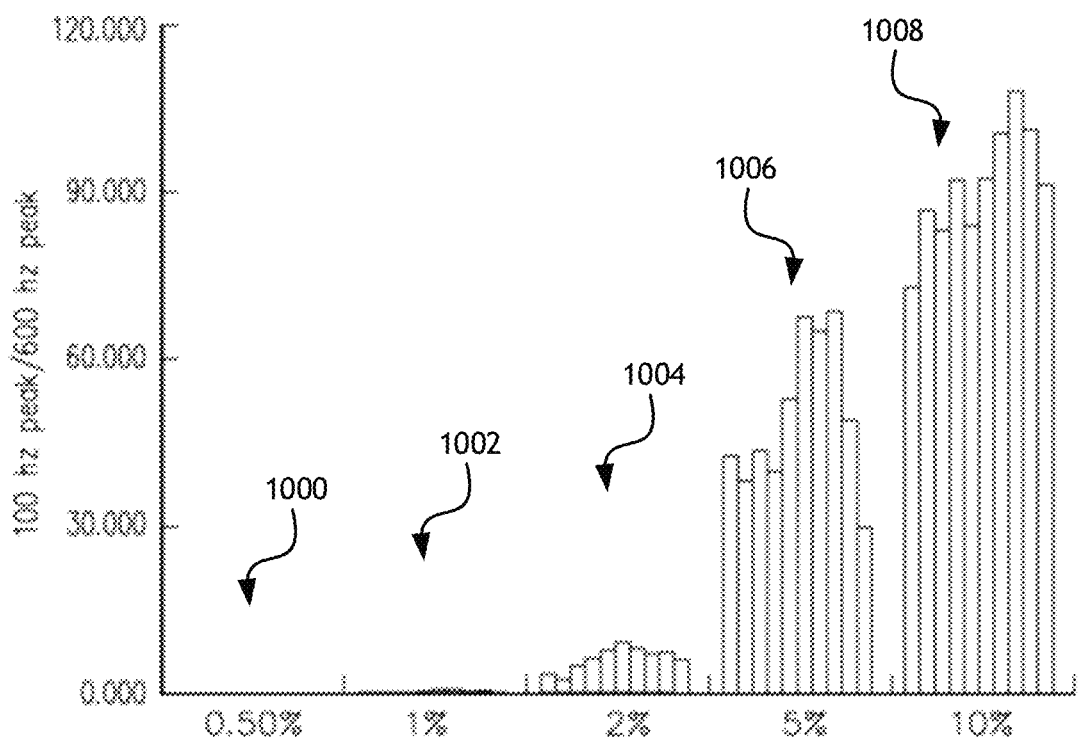
FIG. 10 shows a bar graph of vibration frequencies produced by one embodiment of the present invention in various hydrogel concentrations.

Referring to FIG. 10, a bar graph of vibration frequencies produced by one embodiment of the present invention in various hydrogel concentrations is shown. In ten tests, the vibrational frequencies of hydrogels of 0.5% 1000, 1.0% 1002, 2.0% 1004, 5.0% 1006, and 10% 1008 were measured and found to generally increase as hydrogel concentrations increase.

Figure 11:
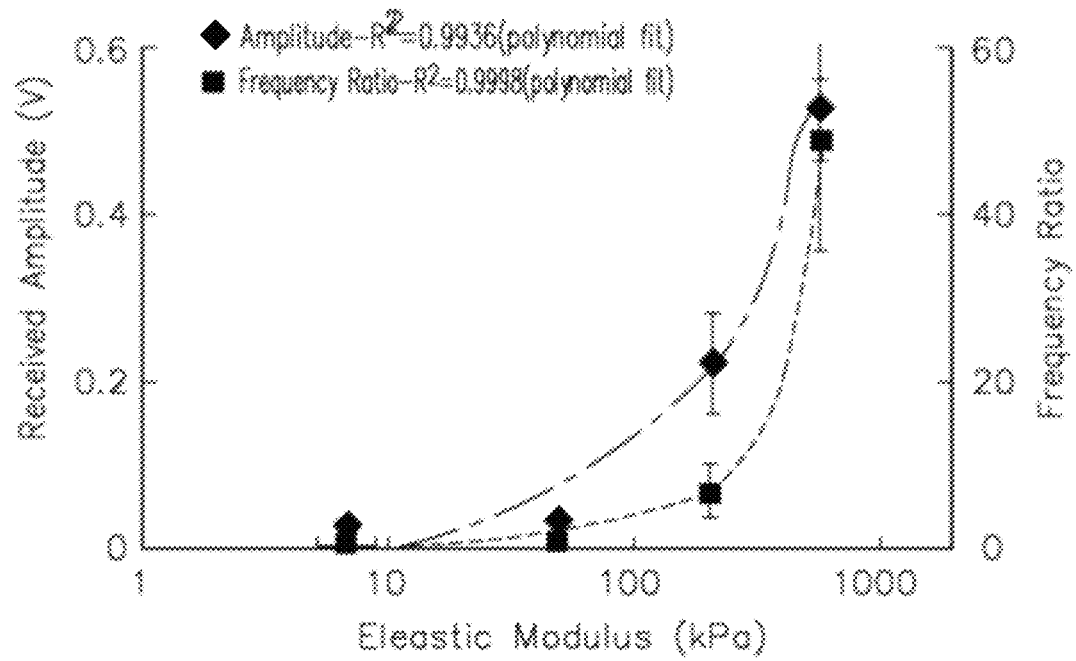
FIG. 11 shows a line graph of amplitude and frequency ratios for various elastic moduli.
Figure 12:
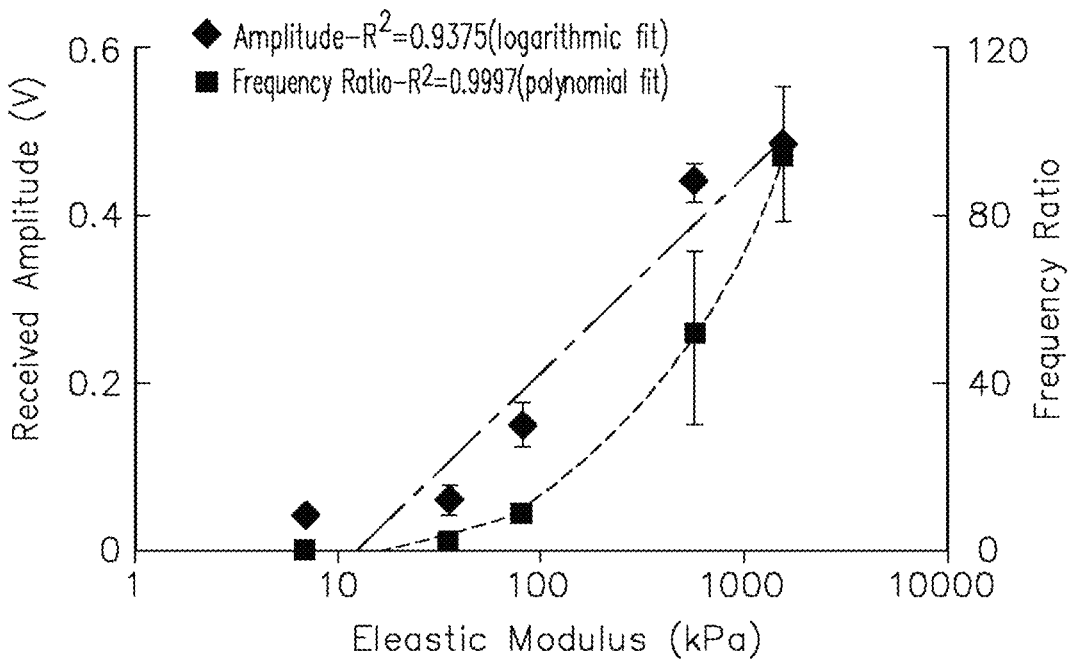
FIG. 12 shows a line graph of amplitude and frequency ratios for various elastic moduli.

Referring to FIGS. 11 and 12, line graphs of amplitude and frequency ratios for various elastic moduli are shown. The correlations indicate the deterministic nature of the approach embodied in the present invention.

Figure 13:
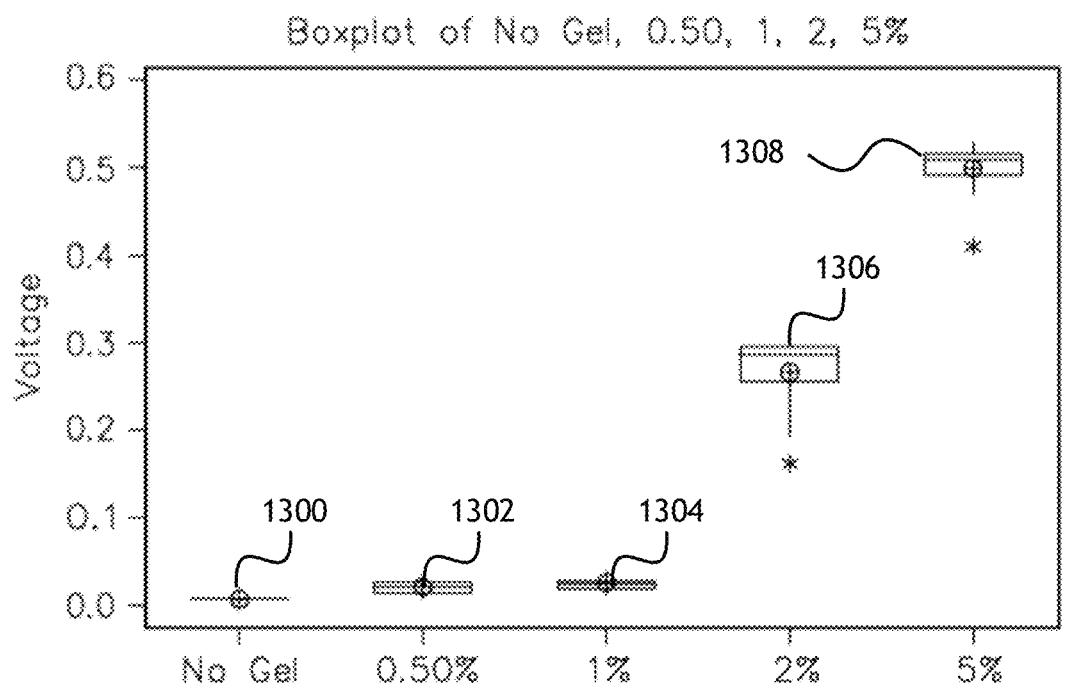
FIG. 13 shows a graph of voltage ranges produced by one embodiment of the present invention in hydrogels at various concentrations.
Figure 14:
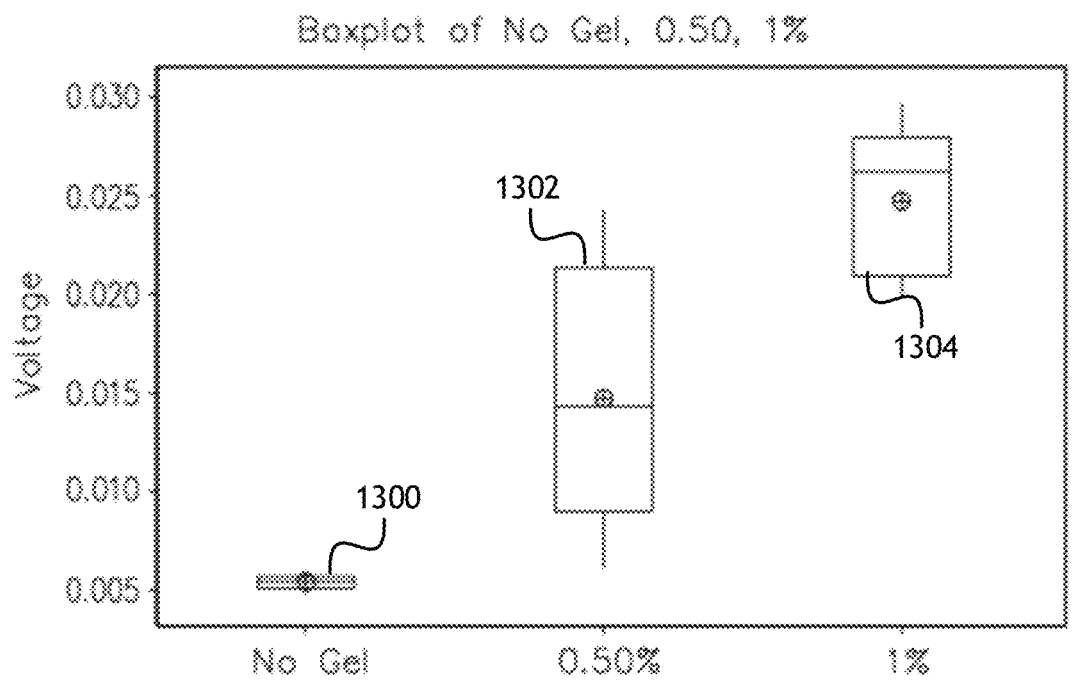
FIG. 14 shows a graph of voltage ranges produced by one embodiment of the present invention in hydrogels at various concentrations.

Referring to FIGS. 13 and 14, graphs of voltage ranges produced by one embodiment of the present invention in hydrogels at various concentrations are shown. Hydrogels show a general increase in voltage produced by one embodiment of the present invention from the lowest voltage range of the control group 1300, through 0.5% 1302, 1.0% 1304, 2.0% 1306 to the highest voltage range at 5.0% 1308. FIG. 14 shows an expanded view of the box plots for the control group 1300, 0.5% concentration 1302 and 1.0% concentration 1304. Hydrogel concentrations are analogous to tissue properties that could be used to determine a tissue type.

Figure 15:
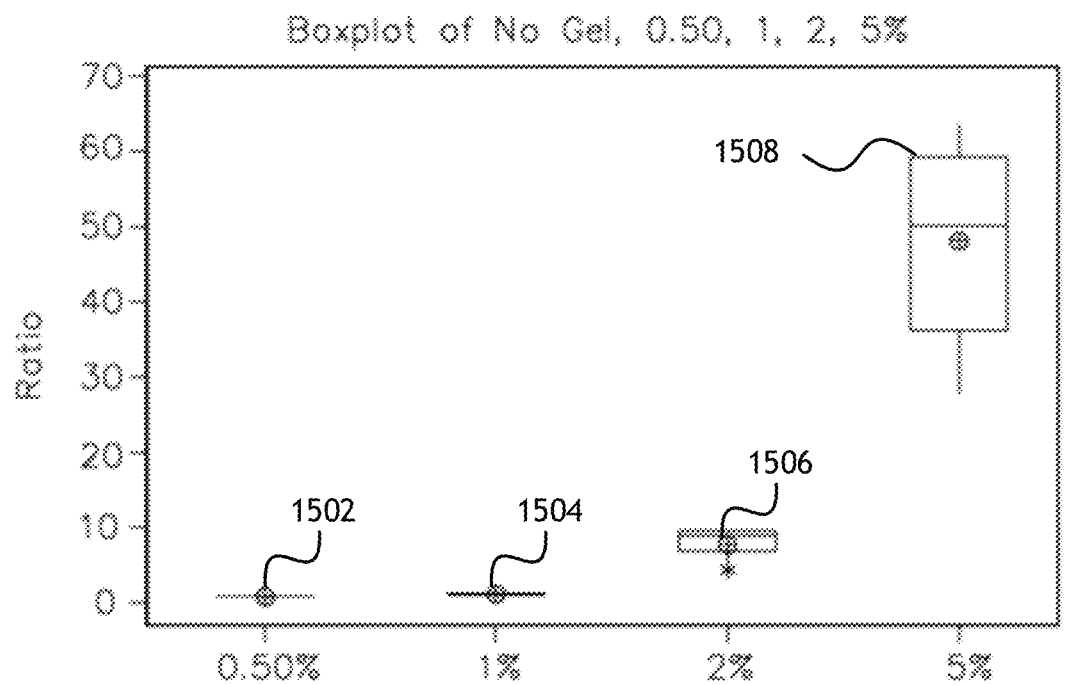
FIG. 15 shows a graph of voltage to frequency ratio ranges produced by one embodiment of the present invention in hydrogels at various concentrations.
Figure 16:
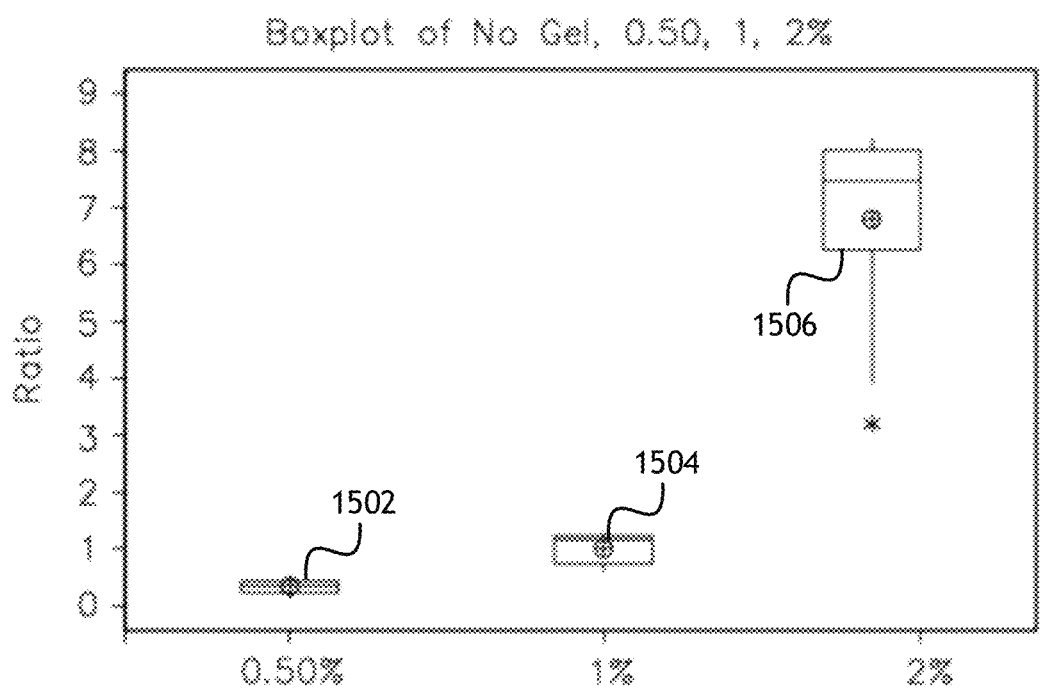
FIG. 16 shows a graph of voltage to frequency ratio ranges produced by one embodiment of the present invention in hydrogels at various concentrations.

Referring to FIGS. 15 and 16, graphs of voltage to frequency ratio ranges produced by one embodiment of the present invention in hydrogels at various concentrations are shown. Hydrogels show a general increase in voltage to frequency ratios produced by one embodiment of the present invention from 0.5% 1502, 1.0% 1504, 2.0% 1506 to the highest voltage range at 5.0% 1508. FIG. 14 shows an expanded view of the box plots for the 0.5% concentration 1502, 1.0% concentration 1504 and 2.0% concentration 1506. Hydrogel concentrations are analogous to tissue properties that could be used to determine a tissue type.

Figure 17:
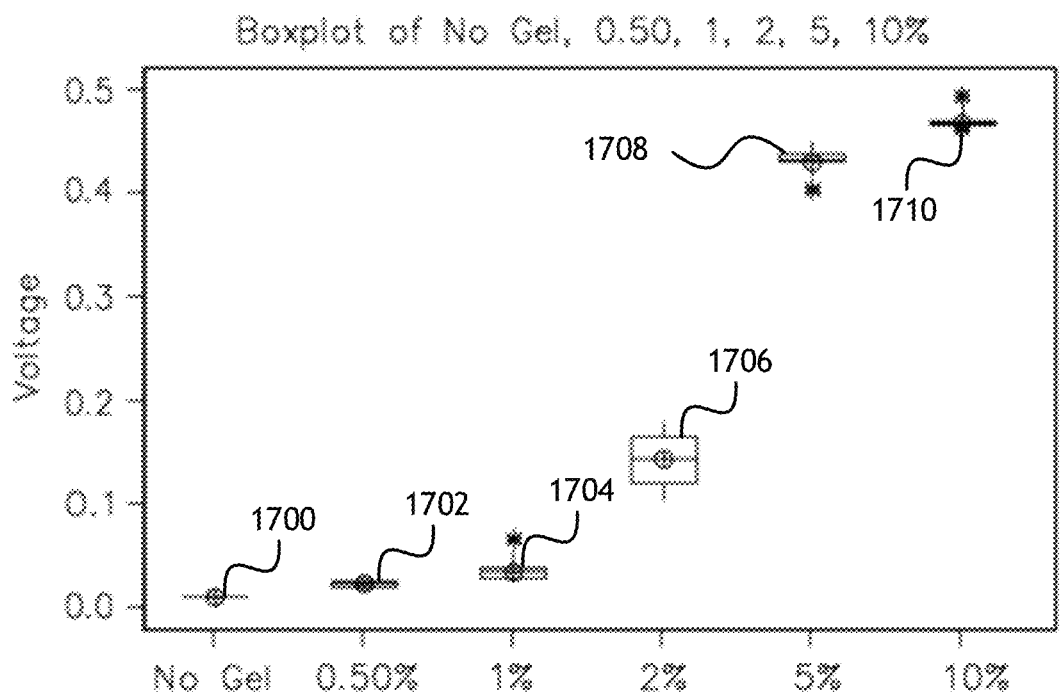
FIG. 17 shows a graph of voltage ranges produced by one embodiment of the present invention in hydrogels at various concentrations.
Figure 18:
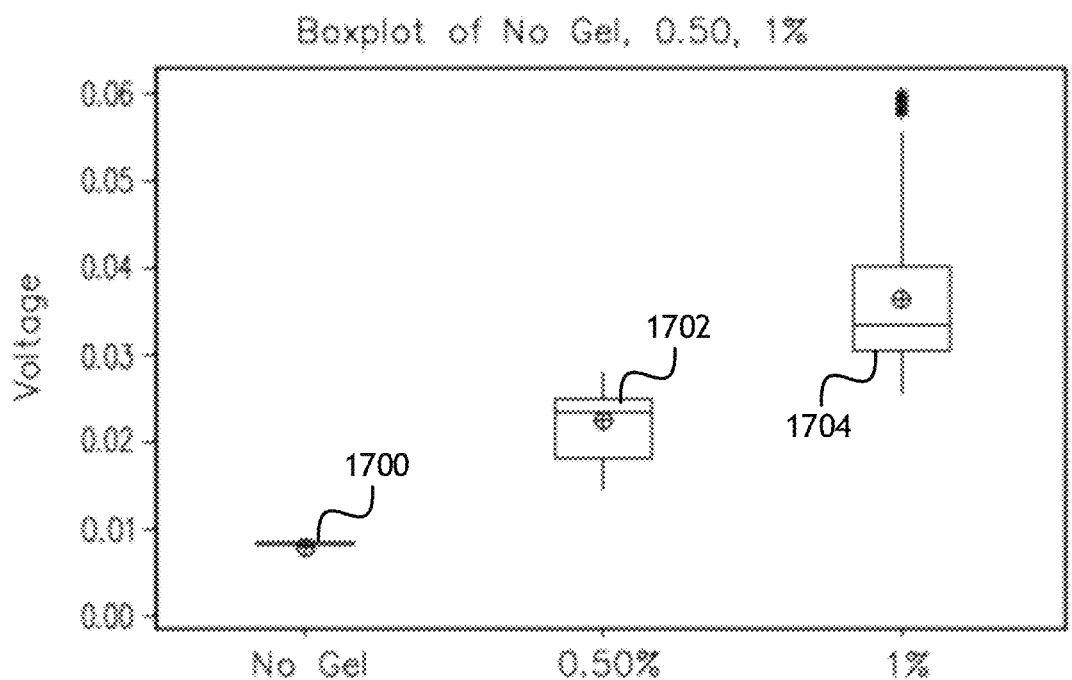
FIG. 18 shows a graph of voltage ranges produced by one embodiment of the present invention in hydrogels at various concentrations.

Referring to FIGS. 17 and 18, graphs of voltage ranges produced by one embodiment of the present invention in hydrogels at various concentrations are shown. Hydrogels show a general increase in voltage produced by one embodiment of the present invention from the lowest voltage range of the control group 1700, through 0.5% 1702, 1.0% 1704, 2.0% 1706, 5.0% 1708 to the highest voltage range at 10% 1710. FIG. 18 shows an expanded view of the box plots for the control group 1700, 0.5% concentration 1702 and 1.0% concentration 1704. Hydrogel concentrations are analogous to tissue properties that could be used to determine a tissue type.

Figure 19:
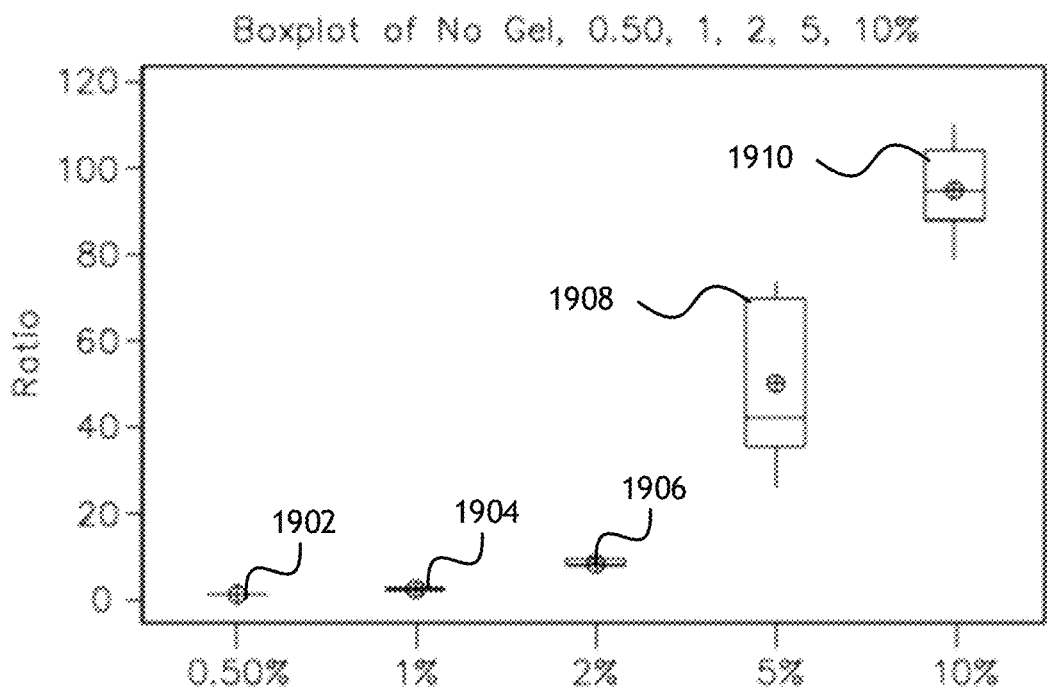
FIG. 19 shows a graph of voltage to frequency ratio ranges produced by one embodiment of the present invention in hydrogels at various concentrations.
Figure 20:
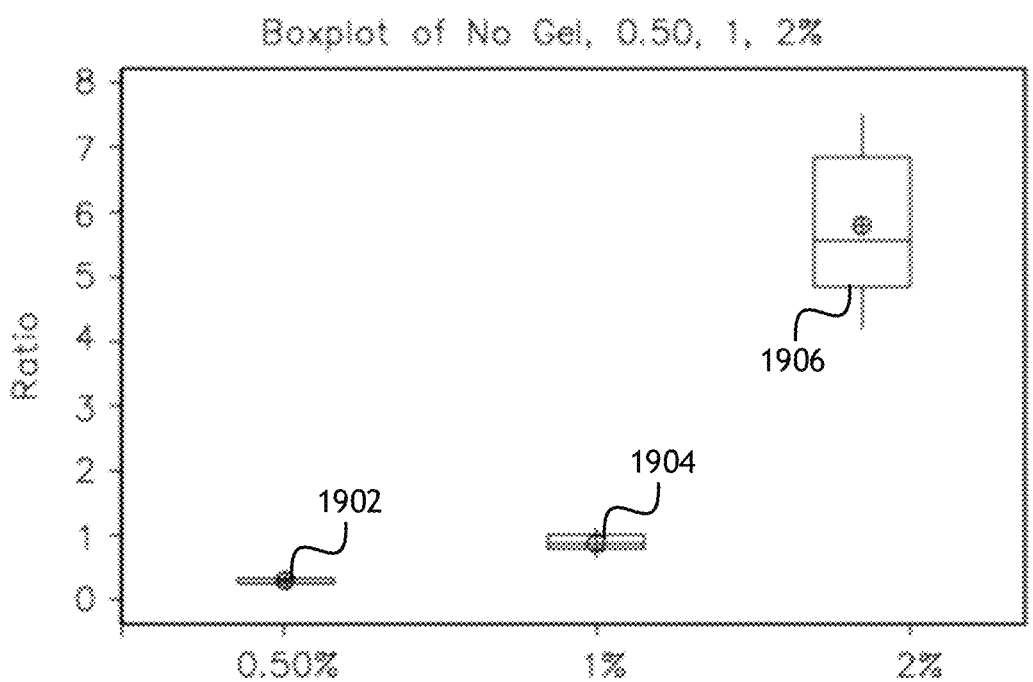
FIG. 20 shows a graph of voltage to frequency ratio ranges produced by one embodiment of the present invention in hydrogels at various concentrations.

Referring to FIGS. 19 and 20, graphs of voltage to frequency ratio ranges produced by one embodiment of the present invention in hydrogels at various concentrations are shown. Hydrogels show a general increase in voltage to frequency ratios produced by one embodiment of the present invention from 0.5% 1902, 1.0% 1904, 2.0% 1906, 5.0% 1908 to 10% 1910. FIG. 20 shows an expanded view of the box plots for the 0.5% concentration 1902, 1.0% concentration 1904 and 2.0% concentration 1906. Hydrogel concentrations are analogous to tissue properties that could be used to determine a tissue type.

It is believed that the present invention and many of its attendant advantages will be understood by the foregoing description of embodiments of the present invention, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A surgical robot comprising:
   a haptic feedback instrument comprising:
   an actuator node comprising a spherical contact tip configured to produce a vibration; and
   a generator node configured to receive a vibration; and
   a processor connected to the actuator node and generator node,
   wherein the processor is configured to:
   induce a vibration by applying an input signal to the actuator node;
   receive an output signal from the generator node via transmission of the vibration transmitted through a tissue;
   determine a tissue type of the tissue based on the output signal;
   determine a signal to apply to a haptic feedback device corresponding to the tissue type; and
   contemporaneously applying the signal to a remote haptic feedback device configured to be used by a surgeon.

2. The surgical robot of claim 1, wherein:
   the actuator node comprises a piezoelectric material configured to vibrate at a known frequency based on the input signal; and
   the generator node comprises a piezoelectric material.

3. The surgical robot of claim 1, wherein the processor is further configured to:
   record the output signal over time; and
   compare output signals to identify a change to the tissue over time.

4. The surgical robot of claim 1, wherein the processor is further configured to produce an audible indication of the tissue type.

5. The surgical robot of claim 1, wherein the processor is further configured to produce a visual indication of the tissue type.

6. The surgical robot of claim 5, wherein the visual indication is incorporated into a streaming video feed.

7. The surgical robot of claim 1, wherein the haptic feedback instrument further comprises an isolating and insulating material for holding the actuator node and generator node in proximity, the isolating and insulating material configured to prevent vibrations from transmitting from the actuator node to the generator node except through mutual contact with the tissue during a surgery.

8. A haptic feedback instrument comprising:
   an actuator node comprising a spherical tip and a piezoelectric material configured to apply a mechanical vibration to a biological tissue sample in a body;
   a generator node comprising a piezoelectric material configured to receive the mechanical vibration transmitted through the biological tissue sample in a body; and
   an isolating and insulating material for holding the actuator node and generator node in proximity, the isolating and insulating material configured to prevent mechanical vibrations from transmitting from the actuator node to the generator node except through mutual contact with the biological tissue sample during a surgery; and
   a processor connected to the actuator node and generator node,
   wherein the processor is configured to:
   induce the vibration by applying an input signal to the actuator node;
   receive an output signal from the generator node via transmission of the vibration transmitted through the biological tissue sample;
   determine a tissue type of the biological tissue sample based on the output signal;
   determine a signal to apply to a haptic feedback device corresponding to the tissue type; and contemporaneously applying the signal to a remote haptic feedback device configured to be used by a surgeon.

9. The haptic feedback instrument of claim 8, wherein the isolating and insulating material is polydimethylsiloxane.

10. The haptic feedback instrument of claim 8, wherein the haptic feedback instrument is configured for use by a surgical robot.

11. The haptic feedback instrument of claim 8, further comprising one or more brackets to isolate the actuator node from the generator node.

12. A computer apparatus comprising:
   a surgical robot;
   a processor remotely connected to the surgical robot;
   memory connected to the processor;
   a data storage element connected to the processor; and
   computer executable program code configured to instruct the processor to:
   induce a vibration in a spherical tip of a piezoelectric actuator node with an input signal;
   receive an output signal from a piezoelectric generator node, the output signal corresponding to a vibration from a biological tissue in contact with the piezoelectric actuator node and the piezoelectric generator node;
   compare the output signal to a set of known signals in the data storage element;
   determine a tissue type for the biological tissue based on the comparison; and
   induce a haptic feedback in a remote haptic feedback device to indicate the tissue type.

13. The computer apparatus of claim 12, wherein the computer executable program code is further configured to instruct the processor to generate a distinct audio signal corresponding to the determined tissue type.

14. The computer apparatus of claim 12, wherein the computer executable program code is further configured to instruct the processor to generate a visual indicator corresponding to the determined tissue type.

15. The computer apparatus of claim 14, wherein the computer executable program code is further configured to instruct the processor to incorporate the visual indicator into a video stream.

16. The computer apparatus of claim 12, wherein the computer executable program code is further configured to instruct the processor to:
   record the output signal over time; and
   compare output signals to identify a change to the biological tissue over time.

17. The computer apparatus of claim 16, wherein the computer executable program code configured to instruct the processor to determine a pulse based on the comparison of output signals.

* * * * *